United States Patent [19]

Comai

[11] Patent Number: 4,535,060

[45] Date of Patent: Aug. 13, 1985

[54] INHIBITION RESISTANT 5-ENOLPYRUVYL-3-PHOSPHOSHIKIMATE SYNTHETASE, PRODUCTION AND USE

[75] Inventor: Luca Comai, Davis, Calif.

[73] Assignee: Calgene, Inc., Davis, Calif.

[21] Appl. No.: 455,634

[22] Filed: Jan. 5, 1983

[51] Int. Cl.$^3$ .................. C12N 15/00; C12N 1/20; C12N 1/00; C12P 19/34

[52] U.S. Cl. .................. 435/172.3; 435/172.1; 435/91; 435/253; 435/317; 435/232; 536/27; 935/14; 935/29; 935/72

[58] Field of Search .............. 435/91, 172.3, 193, 435/253, 317, 240, 879, 183, 232, 172.1, 172.2; 536/27

[56] References Cited

U.S. PATENT DOCUMENTS

| | | | |
|---|---|---|---|
| 3,957,587 | 5/1976 | Armbruster et al. | 435/172.1 X |
| 4,237,224 | 12/1980 | Cohen et al. | 435/172.3 X |
| 4,278,765 | 7/1981 | Debabov et al. | 435/172.3 |

FOREIGN PATENT DOCUMENTS

0035831  9/1981  European Pat. Off. ............ 435/172

OTHER PUBLICATIONS

*Biochemistry of Bacterial Growth* (Eds, Mandelstam et al.), 3rd Ed., pp. 278–282, 1982.
Rogers, S. G. et al., *Appl. Environ. Microbiol.*, vol. 46(1), pp. 37–43, 1983.
Comai, L. et al., *Science*, vol. 221, pp. 370–371, 1983.
Meyers, et al., Journal of Bacteriology, vol. 124(3), pp. 1227–1235 (Dec. 1975).
Roisch et al., Hoppe-Seyler's Zeitschrifft Für Physiological Chemistry, vol. 361(7), pp. 1049–1058, (Jul. 1980).
*Genetic Maps*, vol. 2, Jun. 1982, Stephen J. O'Brien (Ed), Cold Spring Harbor Laboratory, pp. 108–121.

*Primary Examiner*—Thomas G. Wiseman
*Assistant Examiner*—Jayme A. Huleatt
*Attorney, Agent, or Firm*—Bertram I. Rowland

[57] ABSTRACT

Enhanced resistance to glyphosate, an inhibitor of the aromatic amino acid biosynthesis pathway, is imparted to a glyphosate sensitive host. A mutated aroA gene is employed which expresses 5-enolpyruvyl-3-phosphoshikimate synthetase (EC: 2.5.1.19) (ES-3-P synthetase). Methods are provided for obtaining the aroA mutation which provides the enzyme resistant to inhibition by glyphosate, means for introducing the structural gene into a sensitive host, as well as providing a method of producing the enzyme.

The *E. coli* strain C600(pPMG1) has been deposited at the A.T.C.C. on Dec. 14, 1982 and been given A.T.C.C. accession no. 39256.

8 Claims, No Drawings

INHIBITION RESISTANT 5-ENOLPYRUVYL-3-PHOSPHOSHIKIMATE SYNTHETASE, PRODUCTION AND USE

BACKGROUND OF THE INVENTION

1. Field of the Invention

Hybrid DNA technology provides new opportunities for preparing a wide variety of novel compounds having enhanced or unique properties. Cellular life is dependent upon the ability to perform enzyme reactions which provide energy for the cell and produce components essential to the cell's viability. Where a number of cells coexist in relative proximity, it has been frequently of interest to be able to select for one group of cells as against the other group of cells. This mode of selection has found extensive use in hybrid DNA technology in selecting for transformants and transductants.

For the most part, antibiotic resistance has been employed as a marker which is introduced into the cell in conjunction with one or more other structural genes of interest. There are numerous other situations, where one is interested in selecting for cells, where a group of cells is undesired. Coming within such categories are such diverse situations as oncogenesis, where one wishes to selectively destroy tumor cells, in the use of herbicides, where one wishes to select for a crop plant as against a weed, and in therapy against pathogens, where one wishes to destroy an invading microorganism while having minimal effect on the host. The opportunity to introduce DNA in a form where it can express enhanced resistance to a biocidal agent permits one to use enhanced amounts of the biocidal reagents while protecting the host against any detrimental effect from the biocide or biostat.

In those situations, where protection is afforded by producing an enzyme which is insensitive to the biocide or can destroy the biocide, the mutated gene affords a new product which can have a wide variety of useful properties. Enzymes can be used as labels, particularly in diagnostic assays, for the production of products, in assaying for substrates and inhibitors, purification, and the like. The ability to modify an enzyme's specificity can allow for the catalysis of reactions otherwise not available to the enzyme, enhanced activity of the enzyme, or enhanced selectivity of the enzyme.

2. Brief Description of the Prior Art

Hollander and Amrheim, *Plant Physiol.* (1980) 66:823–829; Amrheim et al., ibid. (1980) 66:830–834 and Steinruecken and Amrheim, *Biochem. Biophys. Res. Comm.* (1980) 94:1207–1212, report the biochemical characterization of a target site for glyphosate. This site was identified as a step of the shikimic acid pathway present in plants and bacteria in providing the precursor to aromatic amino acids.

SUMMARY OF THE INVENTION

Novel DNA sequences and constructs are provided which can be used for expression of an enzyme in the shikimic acid pathway, which enzyme has reduced sensitivity to glyphosate. The sequences and constructs can be used for producing the enzyme, which finds use in a wide variety of applications as a label in assays and in the production of its normal product and in providing protection to a cellular host from glyphosate. A method is provided for producing the mutated enzyme.

DESCRIPTION OF SPECIFIC EMBODIMENTS

In accordance with the subject invention, DNA sequences are provided which express a glyphosate resistant enzyme in the shikimic acid metabolic pathway, particularly the enzyme which catalyzes the conversion of phosphoenolpyruvate and 5-phosphoshikimic acid to 5-enolpyruvyl-3-phosphoshikimic acid. The enzyme is 5-enolpyruvyl-3-phosphoshikimate synthetase (EC: 2.5.1.19) (hereinafter referred to as "ES-3-P synthetase"). The structural gene expresses an enzyme which is strongly resistant to glyphosate (N-phosphonomethyl glycine), so that the enzyme is active in the presence of signficant amounts of glyphosate and can impart glyphosate resistance to a glyphosate sensitive cell in which the structural gene can be expressed. DNA constructs are provided which include the structural gene sequence for expression of the glyphosate resistant ES-3-P synthetase, which constructs may be introduced into a variety of hosts in a variety of ways and depending upon the nature of the construct and the host, may be present as an episomal element or integrated into the host chromosome.

The structural gene providing the glyphosate resistant ES-3-P synthetase can be obtained as a mutation in the aroA gene of a glyphosate sensitive host. The host may be mutagenized in a variety of ways, either physically or chemically, and mutants selected by their glyphosate resistance. In addition, mutants may be further selected by cotransduction with aroA, so as to change an aroA auxotroph to prototrophy.

The mutagenized glyphosate resistant hosts are mutagenized a second time and selected at a higher level of glyphosate resistance, as well as the ability to cotransduce to change an aroA$^-$ host to aroA$^+$. The resultant glyphosate resistant hosts are then used to produce a genomic bank, where the intact structural gene may be obtained on fragments of 25 Kb or less. Initially, the genomic bank must be introduced into an appropriate host, so that glyphosate resistance may be selected and the genomic fragment excised from the episomal element for further genetic manipulation to provide for a fragment less than about 5.5 Kb containing the intact structural gene for ES-3-P synthetase.

Once the fragment has been isolated, the fragment or portions of the fragment may then be used as probes for selecting for structural genes providing for glyphosate resistant ES-3-P synthetase. The structural genes of interest will be on fragments of less than about 5 Kb, preferably less than about 2 Kb and will include at least a portion of the aroA structural gene, usually the entire aroA structural gene. The fragment will be able to complement a wide variety of aroA mutations, transferring prototrophy to aroA auxotrophs. The DNA sequence may come from either prokaryotes or eukaryotes. Illustrative prokaryotes and eukaryotes include bacteria such as Salmonella and Escherichia, fungi, such as Aspergillus and yeast, plants, algae, such as green and blue-green algae, etc., particularly cells which are glyphosate sensitive.

The DNA sequence containing the structural gene expressing the glyphosate resistant ES-3-P synthetase may be joined to a wide variety of other DNA sequences for introduction into an appropriate host cell. The companion sequence will depend upon the nature of the host, the manner of introduction of the DNA sequence into the host, and whether episomal maintenance or integration is desired.

For prokaryotic hosts, a wide variety of vectors exist which may be used for introduction of the DNA sequence into a prokaryotic host. DNA sequences include a wide variety of plasmids, such as pBR322, pACYC184, pMB9, pRK290, etc.; cosmids, such as pVK100, or by transduction, using a virus, e.g. P22, etc.

For eukaryotic hosts, a wide variety of techniques may be employed for DNA introduction into the host, such as transformation with $Ca^{++}$-precipitated bare DNA, a plasmid or a minichromosome, which DNA can be replicated and the structural gene expressed in the host, or introduction into the host as the structural gene and flanking regions by direct insertion, e.g. micropipette, whereby the DNA may be integrated into the host genome. Alternatively, episomal elements may be employed, such as tumor inducing plasmids, e.g., Ti, Ri or fragments thereof or viruses, e.g., CaMV, TMV or fragments thereof, which are not lethal to the host, and where the structural gene is present in such episomal elements in a manner allowing for expression of the structural gene. Particularly of interest are fragments having the replication function and lacking other functions such as oncogenesis, virulence, etc.

The first stage of the subject invention is the development of a DNA sequence which is capable of expressing a glyphosate resistant protein which is capable of fulfilling the function of ES-3-P synthetase. An appropriate host is employed which is glyphosate sensitive, can be grown in vitro, and has the capability of expressing the ES-3-P synthetase structural gene to provide the desired enzyme. It is not necessary that the host which is ultimately to be provided with glyphosate resistance be the same as the host which is mutagenized. As already indicated, the glyphosate resistance may be provided as a result of having a stable episomal element or by a recombination event resulting in integration of the structural gene coding for the glyphosate resistant ES-3-P synthetase. Either prokaryotic or eukaryotic hosts may be employed for the mutagenesis, the host being chosen based on its glyphosate resistance, ease of selection, efficiency of growth, and utility of the mutagenized structural gene for use in the ultimate host.

Conveniently, mutagenesis may be achieved by a wide variety of conventional techniques, either physical or chemical. Chemical mutagenic agents include ethyl methanesulfonate, diazo reagents, e.g. N-nitroso, N-methyl glycine, psoralens, etc. Physical mutagenic agents include ultraviolet light, X-rays, etc.

Since the parent cell is glyphosate sensitive, selection can be carried out by selecting for glyphosate resistance. Glyphosate resistance may be as a result of a number of different types of changes in the cell and in order to ensure that the mutagen provides an enzyme which is glyphosate resistant, it is necessary to establish that the mutation has occurred in the aroA gene. This can be achieved by employing cotransduction to an aroA auxotroph and selecting for glyphosate resistance and aroA+.

Cotransduction can be achieved with a wide variety of viruses (including phage) which are capable of transferring DNA from the genome of the host to another host in which the virus is temperate. In this manner, one can transduce a second host, employ an appropriate lysate, and select for the transduced host with glyphosate resistance, as well as aroA prototrophy. The resulting modified cells may now be mutagenized again or as many additional times as desired, repeating the transfers and selecting for continuously enhanced glyphosate resistance. Desirably, a host should be capable of multiplying in the presence of at least about 0.5 mg/ml of glyphosate, preferably in the presence of about 1 mg/ml glyphosate and even more preferred in the presence of at least 1.5 mg/ml glyphosate in a nutrient medium without the presence of aromatic amino acid in the nutrient medium.

When the desired level of glyphosate resistance has been achieved, the mutagenized aroA locus may be isolated and cloned. Depending upon the choice of restriction enzyme, either partial or complete digestion will be employed. Alternatively, one could initially isolate the gene from a genomic library by subcloning employing aroA complementation. The gene could then be mutagenized as described above or by in vitro mutagenesis, changing one or more codons. The mutagenized gene may then be excised and gene fragments isolated.

The resulting fragments may then be cloned employing an appropriate cloning vector. Cloning can be carried out in an appropriate unicellular microorganism, e.g. a bacterium such as *E. coli*. Desirably, one may use a cosmid, where partial or complete digestion provides fragments having about the desired size. For example, the cosmid pVK100 may be partially digested with BglII and may be ligated to the fragments resulting from a Sau3A digestion of the genome of a glyphosate resistant cell. Packaging will insure that only fragments of the desired size will be packaged and transduced into the host organism.

The host organism may be selected for glyphosate resistance and/or aroA+. The recipient strains may be modified to provide for appropriate genetic traits which allow for selection of transductants. In microorganisms, the transductants may be used for conjugation to other microorganisms, using a mobilizing plasmid as required. Various techniques may then be used for reducing the size of the fragment containing the structural gene for the glyphosate resistant ES-3-P synthetase. For example, the cosmid vector may be isolated, cleaved with a variety of restriction endonucleases, e.g. BglII, HindIII, et cetera, and the resulting fragments cloned in an appropriate vector, conveniently the cosmid vector previously used. A fragment of less than about 5.5 Kb, usually less than about 5 Kb, conveniently less than 2 Kb, can be cloned and provide for aroA complementation and the glyphosate resistant ES-3-P synthetase.

The enzyme may be produced from any convenient source, either prokaryotic or eukaryotic. Where secretion is not obtained, the enzyme may be isolated by lysing the cells and isolating the ES-3-P synthetase according to known ways. Useful ways include chromatography, electrophoresis, affinity chromatography, or the like. Conveniently, N-phosphonomethyl glycine may be conjugated through an appropriate functionality, e.g., the carboxyl group to an insoluble support and used as a packing for the isolation of the ES-3-P synthetase. The purified enzyme can be used in a wide variety of ways. It may be used directly in assays for phosphoenolpyruvate, 3-phosphoshikimic acid and for glyphosate. Alternatively, the subject enzyme can find use as a label in diagnostic assays, by being conjugated to an analyte of interest, e.g. a hapten or antigen, as such assays are described in U.S. Pat. Nos. 3,817,837; 3,654,090 and 3,850,752. The methods of conjugation, as well as the determination of the concentration of an analyte are described in extensive detail in these patents, and the appropriate portions of the disclosure are incorporated herein by reference.

The DNA sequence encoding for the glyphosate resistant ES-3-P synthetase may be used in a variety of ways. The DNA sequence may be used as a probe for isolation of wild type or mutated ES-3-P synthetase. Alternatively, the DNA sequence may be used for integration by recombination into a host to provide for the production by the host of glyphosate resistance.

With plant cells, the structural gene may be introduced into a plant cell nucleus by micropipette injection for integration by recombination into the host genome. Alternatively, temperate viruses may be employed into which the structural gene may be introduced for introduction into a plant host. Where the structural gene has been obtained from a source having regulatory signals which are not recognized by the plant host, it may be necessary to introduce the appropriate regulatory signals for expression. Where a virus or plasmid, e.g. tumor inducing plasmid, is employed and has been mapped, a restriction site can be chosen which is downstream from a promoter into which the structural gene may be inserted at the appropriate distance from the promoter. Where the DNA sequences have not been sequenced, one can chew back for various times with a exonuclease, such as Bal31 or restrict. Methods for introducing viruses and plasmids into plants are amply described in the literature. (Matzke and Chilton, J. of Molecular and Applied Genetics (1981) 1:39–49.)

By modifying plants with glyphosate resistant ES-3-P synthetase, one can use glyphosate as a herbicide with a wide variety of crops at concentrations which ensures the substantially complete or complete removal of weeds, while leaving the crop relatively unaffected. In this manner, substantial economies can be achieved in that fertilizers may be more efficiently utilized, and the detrimental effects resulting from the presence of weeds avoided.

The glyphosate resistant mutated ES-3-P synthetase will have a $K_d$ which is at least about 10 fold greater than the wild type enzyme from the host. The specific activity at 28° C. at concentrations of from about 1–10 times $K_m$ for 3-phosphoshikimic acid will be at least about twice for the mutated synthetase as compared to the enzyme from the original strain. At a concentration of $10\times$ Km of 3-phosphoshikimate and $5\times10^{-5}$M glyphosate, the inhibition of the mutated synthetase will be less than half, preferably less than a quarter of the inhibition of the synthetase from the original strain.

The following examples are offered by way of illustration and not by way of limitation.

EXPERIMENTAL

Materials and Methods

Media and Bacterial Strains

The bacterial strains used are listed in Table 1.

TABLE 1

| Designation | Pertinent genotype/phenotype | Origin/reference |
|---|---|---|
| S. typhimurium | | |
| TA831 | aroA + hisF645 | Ames |
| A1 | aroA1 | a |
| A124 | aroA124 | b |
| A148 | aroA148 | a |
| STK1 | aroA+ | P22TTA831 − A1, this work |

TABLE 1-continued

| Designation | Pertinent genotype/phenotype | Origin/reference |
|---|---|---|
| CTF3 | aroA+, Pmg[r] | P22TA831/EMS × A1, this work |
| CT7 | aroA+, Pmg | P22CTF3/EMS + A1, this work |
| E. coli | | |
| HB101 | recA, hsdR | B. Bachmann[c] |
| WA802 | hsdR2, hsdA+ | B. Bachmann |
| SK472 | serB22, zjj-202:Tn10 | S. Kushner |
| AB2829 | aroA hsdR+ | B. Bachmann |
| AB1321 | aroA hsdR+ | B. Bachmann |
| JF568 | aroA hsdR+ | B. Bachmann |
| LCK8 | hsdR2, zjj-202::Tn10 | P1SK472 × WA802, this work |
| LC1 | aroA hsdR2, zjj-202::Tn10 | P1LCK8 × JF568, this work |
| LC2 | aroA hsdR2, zjj-202::Tn10 | P1LCK8 × AB1321, this work |
| LC3 | aroA hsdR2, zjj-202::Tn10 | P1LCK8 × AB2829, this work |
| NS428 | | d |
| NS433 | | d |

[a]Nishioka et al., Genetics (1967) 56: 341–351.
[b]Gollub et al., J. Biol. Chem. (1967) 242: 5323–5328.
[c]Bachmann, E. coli Genetic Stock Center, Dept. of Human Genetics, Yale University, New Haven, Connecticut.
[d]Enquist, L. & N. Sternberg. Meth. Enzymol., 1979, 281–298 (Academ. Pr., NY)

Selection and Testing for Glyphosate Resistance

Glyphosate was added to M9 medium after autoclaving. For selection experiments, a commercial solution of glyphosate was used. Resistant mutants were isolated by plating bacterial suspensions in M9 broth or on M9 solid medium supplemented with varying amounts of glyphosate. The level of resistance achieved by the mutants was scored by three types of tests: a spot test, consisting of toothpicking a small colony from a non-selective to a selective medium; a streak test, consisting of streaking cells on a selective plate to obtain single colonies; and growth curves, to determine the kinetics of growth in liquid medium supplemented with glyphosate.

DNA Transformation and Transduction of Packaged Cosmid DNA

DNA transformation was performed according to Mandel and Higa, J. Mol. Biol. (1970) 53:159–162. Competent cells were stored at −70° C. in 15% glycerol. Cells for transduction of packaged cosmid DNA were grown to late log phase in 1 ml of LB broth supplemented with 0.4% maltose. Cells were pelleted and resuspended in 0.1 ml of 10 mM MgSO4 to which was added 20–100 μl of a packaged cosmid suspension. Phage particles were allowed to absorb to cells for 20 min. at 37° C. Transductants were allowed to express for one hour at 37° C. with aeration in 2 ml of LB broth and subsequently plated on selective medium. Using either type of packaging extract, $2\times10^5$ cosmids/μg of insert DNA were routinely obtained. Biotec preparations were rated at $10^8$ phages/μg of ligated native lambda DNA while the subject extracts were rated at $10^7$.

Enzyme Preparation and Assay for ES-3-P Synthetase

S. typhimurium strains CT7 and STK1 were grown with aeration for 24 hours at 37° C. in M9 broth. Cells were harvested by centrifugation at 4° C., washed twice with M9 salts, resuspended in 0.01M Tris-HCl (pH 8.2) and sheared with a French press at 20,000 psi. The homogenate was centrifuged at 16,000 g for 40 min and the supernatant treated with 2% protamine sulfate (1.0 ml of 2% protamine sulfate for every 35 mg of protein). The precipitate was removed by centrifugation at 18,000×g for 35 min, resuspended and used for enzyme assays. Activity of the enzyme was determined by measuring the rate of release of inorganic phosphate (Heinonen and Lahti, Anal. Biochem. (1981) 113:313–317).

A typical assay mixture contained 150 μmole maleic acid buffer (pH 5.6), 2.88 μmole phosphoenolpyruvate, 4.08 μmole 3-phosphoshikimate and the enzyme fraction in a total volume of 1.5 ml. The reaction was started by addition of the enzyme after pre-incubation of the assay mixture at 37° C. for 5 min. Aliquots were taken at timed intervals and mixed immediately with the reagents for phosphate analysis. The low pH of the reagent (1.25N $H_2SO_4$) terminated enzyme activity.

RESULTS

Isolation of Glyphosate Resistant Mutants Mapping in the aroA Locus

S. typhimurium strain TA831 did not form colonies on solid M9 medium containing more than 200 μg/ml of glyphosate. For initial selection the concentration of 350 μg/ml for screening glyphosate resistant mutants was chosen. Spontaneous mutants appeared at a frequency of $5 \times 10^{-8}$ per cell plated. In none of ten independent mutants tested did glyphosate resistance cotransduce with aroA.

To improve the chances of finding aroA mutants, chemical mutagenesis was employed, as well as an enrichment step in which glyphosate resistant mutants mapping in aroA were selected on 35.0 μg/ml glyphosate by cotransduction. After mutagenesis of S. typhimurium strain TA831 with ethyl methanesulfonate, the frequency of glyphosate resistant mutants was $1 \times 10^{-4}$ per cell plated. Two groups of 10,000 mutants originating from independent mutagenesis experiments were used to prepare a mixed lysate of P22. This was then used to transduce S. typhimurium strain A1. Cells were plated on M9 medium and M9 plus glyphosate. The number of colonies appearing on glyphosate plates was one hundredth of those appearing on M9 alone. None ($< 10^{-3}$) appeared when a phage lysate from unmutagenized strain TA831 was used. Ten glyphosate resistant mutants were tested and all cotransduced with aroA. These results suggest that about 1% of all mutations conferring glyphosate resistance mapped close to, or in, aroA. One of the mutants was chosen for further characterization and was designated strain CTF3. By a spot test it was resistant to 350 μg/ml of glyphosate. A second cycle of mutagenesis was carried out on strain CTF3 to obtain a higher level of resistance to glyphosate. Ten cultures were treated with ethyl methanesulfonate, and plated on 1 mg/ml of glyphosate. Resistant colonies appeared with a frequency of $10^{-6}$ per cell plated. Ten thousand mutants were again pooled for each mutagenesis group and lysates prepared from each pool used to transduce strain A1. Transductants were selected on M9 and M9-supplemented with 1 mg/ml glyphosate. Selection for aroA+ gave $10^{-5}$ transductants per cell plated. Selection for aroA+, glyphosate resistant cells gave a transduction frequency of $10^{-8}$. In fifteen of twenty transductants tested, glyphosate resistance cotransduced with aroA. From these results it was deduced that approximately $1 \times 10^{-3}$ mutations obtained in the mutagenesis of strain CTF3 mapped close, or in, the aroA locus. The phenotype expressed by these mutants is designated Pmg$^r$. No significant difference in resistance levels was detected among fifteen separate mutants. All formed colonies in 48 hours when streaked on M9 medium containing 2 mg/ml of glyphosate. Mutant CT7 was chosen for further characterization. Pmg$^r$ in this strain cotransduced 97–99% of the time with aroA1, aroA126 and aroA248.

Mechanisms of Glyphosate Resistance

Resistance to glyphosate mediated by a mutation(s) at the aroA locus could result from altered regulation leading to overproduction of 5-enolpyruvyl-3-phosphoshikimate synthetase or to a structural alteration of the enzyme. To distinguish between these two hypotheses, in vitro enzyme preparations were assayed from Salmonella strains STK1 and CT7 which are the wild type and mutant strain respectively. 5-Enolpyruvyl-3-phosphoshikimate synthetase activities from wild type and glyphosate resistant mutants differed by Km for 3-phosphoshikimate, $K_d$ for glyphosate, and at high concentration of 3-phosphoshikimate, by specific activity. These results are summarized in Table 2.

TABLE 2[a]

| Source[c] | Specific activity[b] 3-P-shikimate, conc. M | | $K_m$ 3-P-shikimate | $K_d$ glyphosate |
|---|---|---|---|---|
| | $3.4 \times 10^{-4}$ | $3.4 \times 10^{-3}$ | | |
| STK 1 | $0.7 \times 10^{-6}$ | $1.7 \times 10^{-6}$ | $3.4 \times 10^{-4}$ | $2.2 \times 10^{-5}$ |
| CT7 | $1.1 \times 10^{-6}$ | $3.7 \times 10^{-6}$ | $2.8 \times 10^{-3}$ | $1.9 \times 10^{-4}$ |

[a]Enzyme preparations were obtained as described in Materials and Methods. Phosphoenolpyruvate was $2.5 \times 10^{-1}$ M in all assays.
[b]Pi · ml$^{-1}$ · sec.$^{-1}$ · μg protein$^{-1}$.
[c]Cells of the wild type, STK1 and of the glyphosate resistant mutant, CT7, were grown in minimal medium to early stationary phase.

The above assays were performed on enzyme preparations obtained from cells grown in minimal medium. To determine whether the enzyme of the glyphosate resistance mutant was differentially regulated during glyphosate induced stress. STK1, the wild type, and CT7, the mutant, were grown in minimal medium supplemented, respectively, with 70 μg/ml and 1000 μg/ml of glyphosate. These conditions give approximately 20–30% growth inhibition. The specific activity of preparations from cells grown in the presence of glyphosate was 10% higher than that found in preparations from cells grown without glyphosate. This increase in activity was exhibited both by STK1 and CT7 ruling out that in the glyphosate resistant mutant, the enzyme would be overproduced in response to glyphosate.

The growth kinetics of both S. typhimurium and E. coli strains with wild type and mutant aroA locus were investigated. In minimal medium strains of either genus harboring the aroA-Pmg$^r$ allele only exhibited a 15% lower growth rate than the isogenic line harboring either the wild type allele, or both wild type and Pmg$^r$ alleles. At 100 μg/ml glyphosate, wild type E. coli showed 40% inhibition of growth rate. At one mg/ml glyphosate, no growth was observed. The aroA E. coli strain LC3 harboring pPMG1 (to be described subsequently) was not significantly inhibited at 2000 μg/ml of glyphosate.

Cloning of the aroA and aroA Pmg$^r$ Locus

Chromosomal DNA from strain CT7 was partially digested with the restriction endonuclease Sau3A. pVK100, a low copy number, 23 Kb cosmid vector (Knauf and Nester, Plasmid (1982) 8:45–54), was partially digested with BglII to avoid excision of the cos site which is on a BglII fragment. Equal amounts of vector and insert DNA were mixed, ligated, and packaged in lambda capsids as described in Methods. Analysis of random transductants from the bank revealed that 60% of them harbored cosmid DNA of the expected size (45 Kb), consisting of the vector pVK100 and an average chromosomal insert of 20–25 Kb. To isolate the aroA-Pmg$^r$ gene *E. coli* aroA mutants were complemented. Due to the presence of Salmonella DNA the bank did not transduce hsdR+ strains of *E. coli.* Three *E. coli* strains were constructed which were both aroA and hsdR. For this purpose strain SK472, in which zjj202::Tn10 is linked to hsdR+, was used. By transducing zjj202::In10 in strain WA802 and selecting for tetracycline resistant, serine auxotrophic, restriction deficient recombinants, zjj202::Tn10 was linked to the hsdR2 allele. This was introduced into three different aroA mutants by selection for Tn10. The three new strains derived from JF568, AB1321 and AB2829 were, respectively, designated LC1, LC2 and LC3. LC3 was chosen for further experiments since it had the lowest aroA+ reversion rate. After transduction of the Salmonella CT7 DNA bank into strain LC3, 500 kanamycin resistant transductants were screened for growth on minimal medium. Two aroA+ clones were found. When tested for glyphosate resistance they were found to be as resistant as strain CT7. Plasmid DNA was isolated from these clones and both harbored a 45 Kb cosmid which by preliminary restriction endonuclease analysis were found to be similar. One of the two plasmids (pPMG1) was chosen for further characterization.

When introduced by transformation into the appropriate *E. coli* strains, pPMG1 complemented all aroA mutations tested (see Table 1); in addition, it conferred glyphosate resistance to all strains into which it was introduced, either aroA or aroA+. By conjugation, using pRK2013 (Ditta et al., PNAS USA (1980) 77:7347–7351) as a mobilizing factor, pPMG1 was introduced into *S. typhimurium* strains A1, A124 and A148 where it conferred an aroA+ Pmg$^r$ phenotype. Enzymatic characterization of aroA+ *E. coli* transformants confirmed the phenotypic response, since ES-3-P synthetase activity in these strains was indistinguishable from that in strain CT7. It was concluded that the aroA-Pmg$^r$ gene was cloned. The wild type aroA allele was also cloned using a similar protocol. Two cosmids were isolated from a bank of STK1 DNA. They carried a common region of approximately 10 Kb and were designated pAROA1 and pAROA2.

To subclone the aroA-Pmg$^r$ gene, plasmid pPMG1 was digested with the restriction endonuclease BglII. Three insert fragments were found that were 10, 9.6 and 1.6 Kb in size, respectively. Plasmid pPMG1 was digested to completion with BglII, ligated in vitro and the DNA transformed into strain LC2 selecting for aroA complementation. Clones were screened and plasmids containing the 10 Kb BglII fragment in both orientations relative to the vector pVK100 were identified. Plasmids pPMG5 and pPMG6 complemented aroA *E. coli* strains and conferred high levels of glyphosate resistance. Further subcloning was accomplished by digesting plasmid pPMG5 with BglII and HindIII and ligating in vitro. Strain LC2 was transformed and colonies which were aroA+ and kanamycin sensitive were selected. Analysis of plasmids contained in these clones showed a 5.5 Kb BglII/HindIII Salmonella DNA segment that complements aroA *E. coli* strains and confers high levels of glyphosate resistance (approx. 2 mg/ml). This plasmid was designated pPMGII. An electrophoresis gel indicated that plasmids pPMG1, pPMG5 and pPMGII as well as pAROA1 (a plasmid containing the wild type Salmonella aroA+ allele) all contain the 5.5 Kb BglII/HindIII DNA segment.

In accordance with the subject invention, herbicidal resistance can be imparted to a sensitive host to provide for enhanced protection of the cells of the host. In addition, mutant enzymes can be produced which can find utility in a wide variety of situations involving enzymes as labels, for the measurement of various compounds, as well as for the production of products, where the enzyme may be free of inhibition from contaminants which inhibit or interfere with the enzyme catalyzed reaction. In addition, DNA sequences are provided which can be used for probing both wild type and mutated genes expressing ES-3-P synthetase. Furthermore, a method is provided demonstrating a technique for mutating an enzyme in order to modify a selectable property and obtaining genes expressing such an enzyme.

Although the foregoing invention has been described in some detail by way of illustration and example for purposes of clarity of understanding, it will be obvious that certain changes and modifications may be practiced within the scope of the appended claims.

What is claimed is:

1. A culture of cells consisting essentially of cells containing glyphosate resistant 5-enolpyruvyl-3-phosphoshikimate synthetase having at least one mutation originating from in vitro mutation in the aro locus for the structural gene expressing said synthetase, wherein glyphosate inhibition of said synthetase containing said mutation is less than about one-half of the synthetase of the original strain prior to mutation.

2. A culture of cells according to claim 1, wherein said structural gene is on an episomal element.

3. A culture of cells according to claim 2, wherein said cells are prokaryotic.

4. A DNA sequence of less than 5 Kb having a structural gene coding for a glyphosate resistant 5-enolpyruvyl-3-phosphoshikimate synthetase.

5. A DNA sequence according to claim 4, having a mutation originating from in vitro mutation, wherein glyphosate inhibition of said synthetase containing said mutation is less than about one-half of the synthetase of the original strain prior to mutation.

6. A DNA sequence according to claim 5, wherein said synthetase is mutated prokaryotic synthetase.

7. A DNA construct comprising a DNA sequence according to claim 4 and a replication system capable of replication in a cellular host.

8. A DNA construct according to claim 7, wherein said replication system is recognized by a prokaryotic host.

* * * * *